United States Patent [19]

Rosenbaum et al.

[11] Patent Number: 4,723,953

[45] Date of Patent: * Feb. 9, 1988

[54] ABSORBENT PAD

[75] Inventors: Richard J. Rosenbaum, Littleton; Darin D. Pratt, Montrose, both of Colo.

[73] Assignee: Rocky Mountain Medical Corporation, Greenwood Village, Colo.

[*] Notice: The portion of the term of this patent subsequent to Feb. 17, 2004 has been disclaimed.

[21] Appl. No.: 897,077

[22] Filed: Aug. 18, 1986

Related U.S. Application Data

[63] Continuation-in-part of Ser. No. 689,481, Jan. 7, 1985, Pat. No. 4,643,727.

[51] Int. Cl.⁴ ............................................. A61F 13/00
[52] U.S. Cl. .................................. 604/369; 604/374; 604/385 R; 604/378
[58] Field of Search ............... 604/374, 369, 385, 387, 604/365, 378, 384, 366

[56] References Cited

U.S. PATENT DOCUMENTS

| | | | |
|---|---|---|---|
| 2,296,341 | 9/1942 | Fourness | 604/378 |
| 2,464,640 | 3/1949 | Fourness | 604/378 |
| 2,548,341 | 4/1951 | Bricmont | 604/378 |
| 2,600,576 | 6/1952 | Rickard et al. | 604/378 |
| 3,468,311 | 9/1969 | Gallagher . | |
| 3,563,242 | 2/1971 | Hedstrom | 604/378 |
| 3,592,194 | 7/1971 | Duncan . | |
| 3,800,797 | 4/1974 | Tunc | 604/378 |
| 3,812,001 | 5/1974 | Ryan . | |
| 3,881,491 | 5/1975 | Whyte . | |
| 3,886,941 | 6/1975 | Duane et al. . | |
| 3,889,679 | 6/1975 | Taylor . | |
| 4,055,180 | 10/1977 | Karami . | |
| 4,333,463 | 6/1982 | Holtman | 604/378 |
| 4,360,015 | 11/1982 | Mayer . | |
| 4,443,512 | 4/1984 | Delvaux | 604/379 |
| 4,534,769 | 8/1985 | De Jonckheere et al. | 604/369 |

Primary Examiner—C. Fred Rosenbaum
Assistant Examiner—Denise Whelton
Attorney, Agent, or Firm—Fields, Lewis, Pittenger & Rost

[57] ABSTRACT

An absorbent pad is provided which includes an absorbent layer which serves as a reservoir for liquid and has a liquid impervious barrier over one surface thereof. The liquid is applied to the opposite surface of the barrier and is conducted by means of wicking material to the sides of the barrier and into the absorbent layer. This arrangement enhances drying of the upper surface of the barrier and wicking material shortly after application of the liquid. A hydrophobic porus of open weave material can be provided over the wicking material to protect it and to provide a surface through which the liquid can reach the wicking material and the barrier sheet. The barrier sheet can have multiple channels formed in the liquid receiving surface thereof to disperse the liquid toward the edges thereof.

17 Claims, 8 Drawing Figures

ABSORBENT PAD

This application is a continuation-in-part of co-pending application Ser. No. 689,481 field 1-7-85, now U.S. Pat. No. 4,643,727, issued 2-17-87.

TECHNICAL FIELD

The present invention relates to an improved absorbent pad, and more particularly to a diaper, having a moisture impervious membrane for receiving liquid on one side, which is covered by a wicking material to transfer the liquid rapidly to a reservoir on the other side so that the membrane and wicking material rapidly becomes substantially dry between wettings.

BACKGROUND ART

Other inventors have tried to solve these problems without complete success, such as U.S. Pat. No. 3,468,311 to Gallagher, which is directed to an absorbent pad having an air bubble layer in which are provided a plurality of liquid permeable perforations to provide a passageway for fluids therethrough to a lower highly absorbent layer. The absorbent pad comprises a pneumatic cellular cushion top layer, a liquid absorbent layer and a bottom liquid impervious layer. The uppermost layer comprises a pneumatic cellular cushion layer and the bottom layer comprises a liquid impervious plastic sheet with a highly absorbent layer in between the cushion layer and the impervious plastic layer. This top-most layer comprises a pair of plastic sheets assembled to provide a plurality of air or other fluid filled cells which cells are spaced from each other by partition zones formed by sealing opposed surfaces of the sheets together. Between the cells and in the partition walls are a plurality of perforations large enough to permit generally unrestricted liquid flow from the cushion layer to the absorbent layer.

U.S. Pat. No. 4,360,015 to Mayer is directed to a multilayer absorbent structure having two absorbent layers separated by a grid material and covered on one side by an exterior layer which contacts a wound surface and on the other side by a moisture resistant barrier. The outer wound contacting layer adjacent the absorbent layer may be unwoven. The next grid layer is non-absorbent but has openings through the grid through which fluids to be absorbed passes. The next layer is absorbent material while the exterior layer is a fluid barrier.

U.S. Pat. No. 4,055,180 to Karami discloses an absorbent pad having a perforated impervious sheet for conducting liquid into spaced pockets containing absorbent material.

U.S. Pat. No. 3,812,001 to Ryan discloses an absorbent pad having a plurality of interspersed air blisters which minimize the compression of the pad by the weight of the user so that it can absorb more liquid.

U.S. Pat. No. 3,881,491 to Whyte has a plurality of spaced inflatable areas which are activated by moisture for expanding the pad so that it will absorb more material and for supporting the body of the user so that it does not become compressed, thereby absorbing more liquid.

U.S. Pat. No. 3,889,679 to Taylor discloses a diaper having a plurality of openings for conducting the fluid to the outer portion of the absorbent material to increase utilization of the absorbent material for rapid dispersion of the liquid.

U.S. Pat. No. 3,886,941 to Duane, et al. discloses an absorbent pad having a fluid impervious outer layer which has uniform slots spaced thereacross through which the fluid will flow toward an absorbent pad therebelow, but is restrained from back flow through the slots.

U.S. Pat. No. 3,592,194 to Duncan discloses in the embodiment of FIG. 8 an absorbent material which is attached to an impervious bottom layer and has an open weave hydrophobic material over the top thereof. Within the absorbent material and spaced from the upper surface thereof is a moisture impervious barrier sheet spaced below the hydrophobic sheet. This diaper improves dryness of the diaper against the baby's skin to some extent, but since the material above the barrier is also liquid absorbent, it will always tend to remain damp and will not effectively wick the liquid away from the barrier so that the hydrophobic material becomes dry.

Although each of the above prior art devices is suitable for its intended purpose, none of them provide a structure wherein liquid is temporarily stored on top of a non-permeable barrier or sheet while the wicking material pulls the moisture around the barrier and stores it in a reservoir on the other side of the barrier allowing the wicking material and exposed barrier surface to dry.

DISCLOSURE OF THE INVENTION

In accordance with this invention, an absorbent pad is provided which becomes substantially dry after wetting. This pad includes a liquid receiving membrane, a liquid reservoir for storing liquid applied to the membrane, an impervious means separating the membrane from the reservoir and wick means for conducting the liquid from the membrane to the reservoir, the liquid impervious means substantially preventing liquid in the reservoir from returning to the membrane. More specifically, the wicking means comprises a sheet of wicking material which substantially envelops the liquid impervious means which is a layer of liquid impervious material that is coextensive with the membrane. The impervious layer and the membrane have substantially coextensive side edges so that the wicking sheet can draw the liquid from the liquid receiving membrane around the side edges of the impervious layer into the reservoir. The reservoir is substantially coterminous with the sheet of wicking material and comprises an absorbent layer coextensive with the impervious layer and an outer layer of liquid impervious material coextensive with the absorbent layer to retain liquid in the absorbent layer between it and the impervious layer.

With applicant's invention, when liquid is intermittently released onto the pad, it is supported by the impervious membrane until it can be transferred by the wick around the edges of the membrane and into the reservoir. The membrane prevents any substantial back flow of fluid from the reservoir to the other side of the barrier so that the membrane and barrier facing the body of the user can dry. Furthermore, the user's weight on the pad, while having a compressing effect on the material in the reservoir, will not cause the liquid to back flow around the barrier since the only path for such back flow would be through the wick. Even if some back flow occurred around the edges of the wick, this would not be the portion of the pad which is directly against the body of the user.

Additional advantages of this invention will become apparent from the description which follows, taken in conjunction with the accompanied drawings.

BEST MODE FOR CARRYING OUT THE INVENTION

Figure 1:
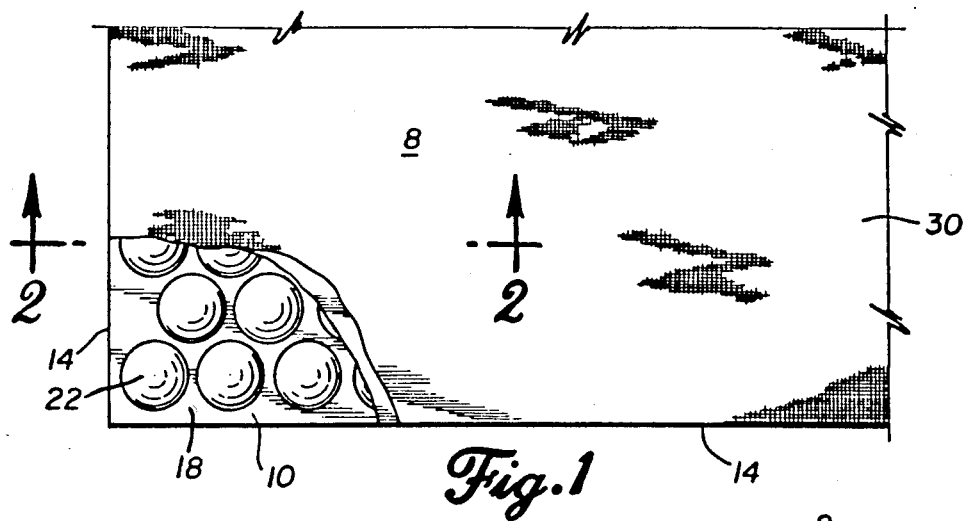
FIG. 1 is a top plan view of one form of an absorbent pad, such as a diaper, having an impervious barrier which includes spaced bubbles constructed in accordance with the teachings of the present invention with portions broken away for clarity of illustration.
Figure 2:
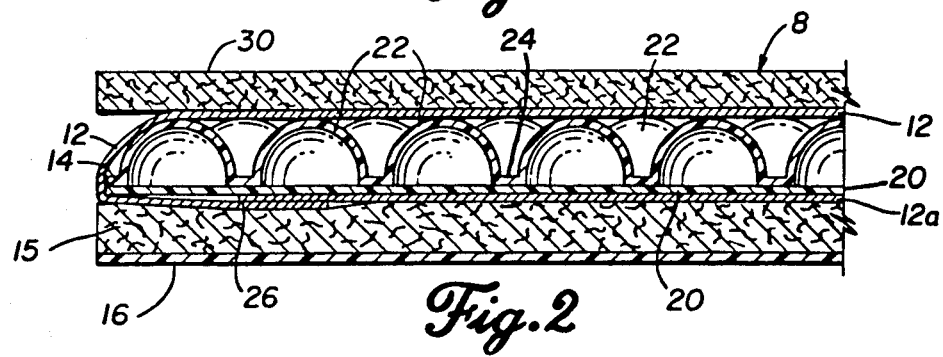
FIG. 2 is a horizontal section, taken along line 2—2 of FIG. 1, showing further details of the absorbent pad.
Figure 3:
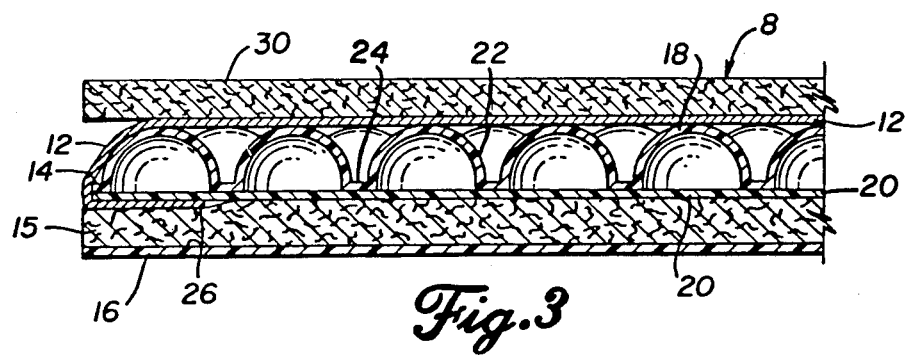
FIG. 3 is a horizontal section, similar to FIG. 2 of another form of the present invention.

Referring to the drawings, the improved diaper 8 is comprised of at least four layers. The uppermost layer generally designated as 10 comprises an air cell cushion layer. A highly absorbent wicking layer 12 completely covers the top of the air cells of the air cell layer and is wrapped around at least an opposing pair of sides 14 of the air cell layer. Immediately beneath the folded under portions of the wicking layer 12 is an absorbent layer 15 of wadding and the like and the bottom layer 16 is a liquid impervious plastic layer.

The uppermost layer 10 comprises a pair of liquid impervious plastic sheets 18 and 20 sealed together to form a plurality of air bubbles or cushions 22. The air bubbles are separated from each other by sealed zones 24 formed by sealing opposed portions of the sheets 18 and 20 together. Preferably the air bubbles 22 are uniformly spread about the top layer and provide a highly desirable cushion effect. The air bubbles 22 are located and present in such numbers that the uncontrolled flow of liquid onto the top layer is divided and spaced evenly over the top layer so that the liquid will not overflow the edges of that layer.

The wicking layer 12 is positioned on top of the air bubble layer 10 and is folded over at least one pair of edges or sides 14 and preferably all sides 14 of the air bubble layer 10. The folded over portion 26 of the layer 12 may extend inwardly only a short distance but preferably will cover all of the lower surface of the air bubble layer 10 as well.

The wicking layer 12 may be of paper toweling and the like in which a liquid will migrate very rapidly to the marginal edges of the air bubble layer 10 and over the edges 14 to a lower absorbent layer.

The absorbent layer 15 may comprise substantially any of the highly absorbent material or synthetic fibers, woven, non-woven or porous materials. Good results have been obtained by the use of mats or batts of synthetic fibers, mixtures of synthetic fiber, nonwoven cellulosic batts or open cell sponge-like sheets. In a specific embodiment of the present invention the absorbent layer 15 comprised cotton wadding.

The absorbent layer 15 may comprise a mat or mass of hydrophobic fibers wherein the liquid retaining function of the batt takes place along the large surface area of the fibers. Non-water wetting fibers such as Dacron and Nylon have the characteristic property of being non-water absorbent from the standpoint that water generally does not penetrate the fibers; however, such fibers have the characteristic of permitting fluids to wick along their surface and in that manner a batt of such fibrous material will retain or hold a large quantity of liquid on its large surface area when disposed in batt arrangement.

The bottom layer 16 of the diaper preferably is comprised of a thin layer of water impervious plastic such a polyethylene, polypropylene and the like. The primary function of the layer 16 is to provide a barrier for liquids contained in the layer 15. Thus, layer 15 acts as a reservoir for the liquid.

Figure 4:
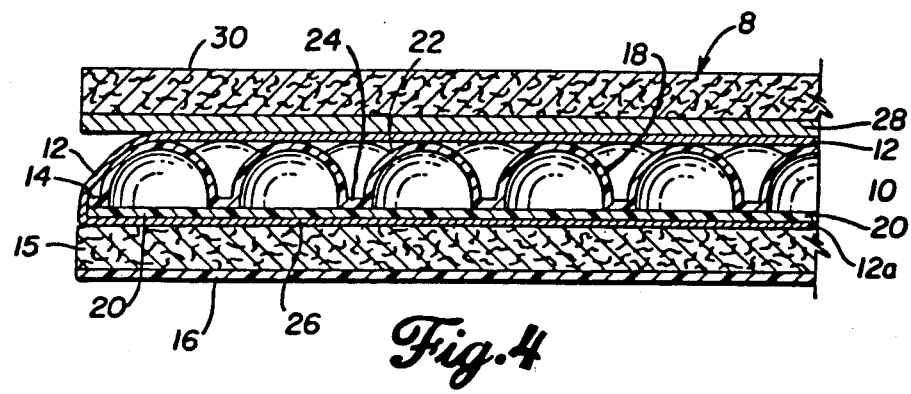
FIG. 4 is a horizontal section, similar to FIGS. 2 and 3 of still another form of the present invention.

As best seen in FIG. 4, the preferred embodiment of the present invention comprises an uppermost layer 28 of Pellon. The next layer 30 is cellulose tissue. The wicking layer 12 is of paper toweling which completely surrounds the air bubble layer 10 having a cushion function. The absorbent layer 15 is of cotton wadding and the bottom layer 16 is of plastic.

In use, the embodiment shown in FIG. 4 receives liquids via the cellulose tissue layer 30 which transfers the excess liquid to a Pellon layer 28. The excess liquid from layer 30 is delivered to the Pellon layer 28 and then to the upper paper towel wicking layer 12 which wicks some of the liquid around the edges 14 of the air bubble layer 10 while the bulk of the liquid is delivered by the upper wicking layer 12 to the air bubble layer 10. The air bubbles 22 projecting upwardly present a barrier pattern to the incoming liquid and breaks the liquid stream into a multitude of small streams or riverlets which migrate to the edges 14 and discharge into the lower wicking layer 12a for even discharge across the surface of the absorbent layer 15. The bottom layer 16 prevents liquids from escaping the absorbent layer.

Figure 5:
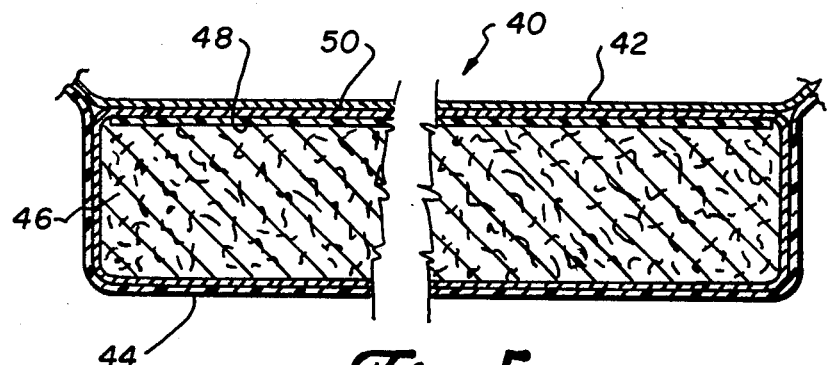
FIG. 5 is a fragmentary horizontal section of still another form of the present invention having a flat barrier sheet with the wicking material extending entirely around the barrier and an absorbent material in the reservoir.

An alternative absorbent pad 40 is disclosed in FIG. 5. It will be understood that this pad can be used as a diaper but also can be used in any situation where it is important to transmit body fluids away from the body so that it and the adjacent portion of the pad can dry. An example of this is feminine hygiene products. This is accomplished by providing a reservoir which is separated from the body by a moisture impervious sheet. As illustrated, it will be understood that the upper surface of the pad is that which contacts the body and the lower surface is away from the body. The upper surface comprises a layer 42 of open weave hydrophobic material which allows the moisture to pass through but does not absorb any of it. This layer is connected along its side edges to an outer layer 44 made of moisture impervious material, such as plastic. Within the space formed by layers 42 and 43 is a thick absorbent layer 46, which may be made of pulp or a pulp-polymer combination to serve as a reservoir for absorbing liquid which is intermittently deposited on hydrophobic layer 42, as will be described below. Above absorbent layer 46 is a barrier sheet 48 which may be made of a moisture impervious plastic that is essentially coterminus with the upper surface of the absorbent layer 46. Between barrier sheet 48 and upper layer 42 is a wicking tissue 50 which extends around the sides edges of barrier sheet 48 and, as shown, can extend entirely around the absorbent layer 46.

From the foregoing, it will be appreciated that as liquid is intermittently deposited on outer hydrophobic layer 42 it will pass therethrough and be held by barrier 48. The wicking material 50 will conduct the liquid by capillary action around the edges of barrier 48 into the reservoir formed by absorbent layer 46. Thus, the outer layer 42 and wicking material 50 over barrier 48 will substantially dry out during the periods of time between the intermittent wetting of the pad. Furthermore, the liquid in absorbent layer 46 will not contact the body because of barrier sheet 48 and even when the pressure of the body against the pad tends to compress absorbent layer 48, the liquid cannot readily get back to the top side of the barrier. There may be some increased wetting along the edges of the pad but this would be in areas which are not in contact with the body, and therefore are not as likely to cause rash or discomfort to the body of the user of the pad.

Figure 6:
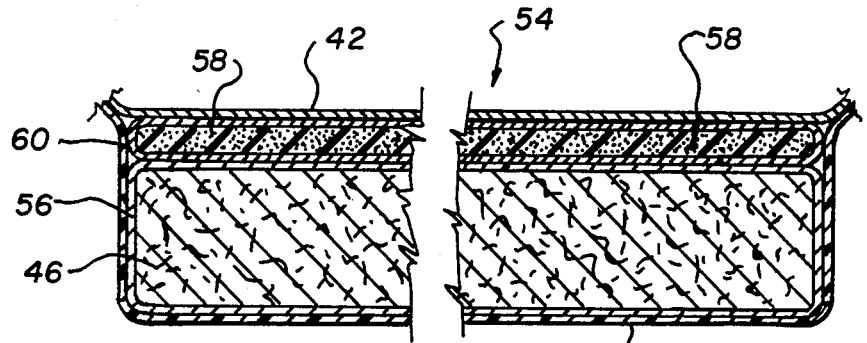
FIG. 6 is a horizontal section, similar to FIG. 5 wherein the wicking material envelops the barrier layer and a separate wicking material envelops the absorbent material in the reservoir.

A further alternative absorbent pad 54 is shown in FIG. 6. This pad includes an upper hydrophobic layer 42 and an outer layer 44 made of moisture impervious material, such as plastic. Within this structure is an absorbent layer 46 which is enveloped by a wicking tissue 56 extending around absorbent layer 46. A barrier sheet 58 is positioned between top layer 42 and the top surface of wicking tissue 56. This barrier sheet is substantially coextensive with absorbent layer 46 and has a second wicking tissue 60 extending around and enveloping it. Conveniently, the barrier sheet is made of a moisture impervious material and is shown as being made of styrofoam so that it will have a greater cushioning effect than the barrier sheet 48 of the previous embodiment. However, in both instances the barrier sheets serve the same purpose.

In the embodiment of FIG. 6, when the liquid is deposited on hydrophobic layer 42, it will pass through the openings therein and be retained by barrier sheet 58 whereupon wicking material 60 will immediately begin transferring the liquid by capillary action around the edges of the barrier sheet and onto the wicking tissue 56 around absorbent pad 46. The wicking tissue 56 will transfer the liquid around an absorbent layer 46 so that it can be absorbed and retained in absorbent layer 46 as a reservoir. This arrangement is designed to enhance the absorption of liquid by absorbent layer 46 due to the layer contact surface with wicking tissue 56.

Figure 7:
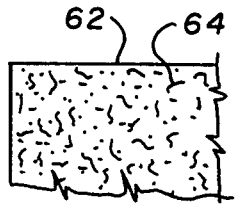
FIG. 7 is a fragmentary plan view of a barrier sheet having an embossed surface.

Another form of barrier sheet 62 is shown in FIG. 7 wherein the upper surface includes embossing 64 thereon to breakdown the liquid into riverlets that will flow in all directions to the outside edge of the barrier sheet to be carried by the wicking material to the absorbent layer 46, as described.

Figure 8:
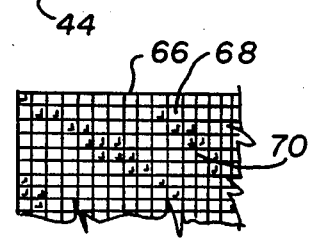
FIG. 8 is a fragmentary plan view, similar to FIG. 7, but showing a barrier sheet having a waffled surface.

A still further embodiment of a barrier sheet 66 is shown in FIG. 8, which includes waffling 68 forming grooves 70 to carry the liquid along the diverse paths to the edge of the sheet.

With the foregoing description, it is seen that the present invention has accomplished the objectives desired with a non-complicated inexpensive structure with superior control of liquids within an absorbent pad.

From the foregoing, the advantages of this invention are readily apparent. In each embodiment, a liquid impervious barrier is provided above an absorbent pad which serves as a reservoir. This pad can take many forms but is enveloped by a wicking material, which by capillary action, carries the liquid to the edges of the barrier and into the absorbent layer. In one embodiment, the barrier is in the form of spaced air cells that provide paths for the liquid to be diverted toward the side and also keep the body of the user away from the liquid. In another embodiment, the barrier sheet is a flat liquid impervious sheet. In another embodiment it is made of styrofoam, and in other embodiments the surface thereof can be embossed or waffled to provide diverse paths for conducting the liquid to the sides of the sheet. With the arrangement disclosed, upon wetting the wicking material immediately moves the liquid to the edges of the pad and into the absorbent layer which serves as a reservoir. The barrier sheet keeps the liquid in the reservoir from migrating back to the side of the barrier sheet against the body of the user. Thus, between liquid applications, the top surface of the barrier and the adjacent tissue, as well as the hydrophobic open weave material have a chance to dry, so that the body of the user also dries and the chances of developing a rash are minimized and the comfort to the user is enhanced.

This invention has been described in detail with reference to particular embodiments thereof, but it will be understood that various other modifications can be effected within the spirit and scope of this invention.

We claim:

1. An absorbent pad having a liquid receiving surface for receiving intermittent applications of liquid and returns to a substantially dry condition shortly after each application of liquid, said pad comprising:
   a first pervious liquid receiving sheet made of fiberous material through which the liquid can pass, said first sheet having an outer liquid receiving surface and an inner surface;
   a second substantially imperforate sheet which is coextensive with said first sheet and impervious to liquid; said second sheet having an outer surface contiguous to said inner surface of said first sheet, an inner surface and side edges;
   a sheet of wicking material which extends over substantially said entire outer surface of said second sheet and around at least some of said side edges thereof, said wicking material being in coextensive contact with said inner surface of said first sheet to transfer liquid applied to said first sheet around the side edges of said second sheet; and
   a reservoir which is coextensive with said inner surface of second sheet to retain liquid conducted to it by said wicking material to return said first sheet to substantially dry condition shortly after each intermittent application of liquid.

2. An absorbent pad, as claimed in claim 1, wherein: said sheet of wicking material substantially envelops said imperforate sheet.

3. An absorbent pad, as claimed in claim 1, wherein said reservoir comprises:
   a absorbent layer coextensive with said inner surface of said imperforate sheet; and
   an outer layer of liquid impervious material extending around said absorbent layer to retain liquid in said absorbent layer between it and said imperforate sheet.

4. An absorbent pad, as claimed in claim 1, wherein:

said imperforate sheet has a plurality of channels formed in its inner surface to disburse liquid thereon toward said side edges.

5. An absorbent pad, as claimed in claim 4, wherein: said inner surface of said imperforate sheet is embossed.

6. An absorbent pad, as claimed in claim 4, wherein: said inner surface of said imperforate sheet is styrofoam.

7. An absorbent pad, as claimed in claim 4, wherein: said inner surface of said imperforate sheet is waffled.

8. An absorbent pad, as claimed in claim 4, wherein: said inner surface of said sheet includes spaced bubbles.

9. An absorbent pad having a surface which becomes substantially dry after wetting, said pad comprising:
   a liquid receiving membrane;
   a liquid reservoir for storing liquid applied to said membrane;
   liquid impervious means separating said membrane from said reservoir; and
   wick means for conducting the liquid from said membrane to said reservoir, said liquid impervious means substantially preventing liquid in said reservoir from returning to said membrane.

10. An absorbent pad, as claimed in claim 9, wherein said wick means comprises:
   a sheet of wicking material which extends around the side edges of said liquid impervious means.

11. An absorbent pad, as claimed in claim 10, wherein:
   said impervious means is a layer of liquid impervious material which is coextensive with said membrane, said impervious layer and said membrane having substantially coextensive side edges, so that said wicking sheet can draw the liquid from the liquid receiving membrane around said side edges of said impervious layer into said reservoir.

12. An absorbent, as claimed in claim 11, wherein:
   said reservoir is substantially coterminus with said sheet of wicking material.

13. An absorbent pad, as claimed in claim 10, wherein:
   said sheet of wicking material extends around said layer of liquid impervious material and said reservoir.

14. An absorbent pad, as claimed in claim 9, wherein said wick means comprises:
   a first sheet of wicking material which substantially envelopes said liquid impervious means; and
   a second sheet of wicking material in contact with said first sheet and which substantially envelops said reservoir.

15. A method of maintaining a liquid receiving membrane in substantially dry condition between intermittent applications of liquid thereto, said method comprising the steps of:
   providing a reservoir for collecting liquid from the membrane;
   rapidly conducting liquid from the membrane to the reservoir upon application of liquid thereto.

16. A method, as claimed in claim 15, including the further step of:
   providing a liquid impervious barrier between the reservoir and the membrane to minimize any back flow of liquid from the reservoir to the membrane.

17. A method, as claimed in claim 15, including providing a wick having a surface which is substantially coextensive with and in contact with the membrane for conducting the liquid from the membrane to the reservoir.

* * * * *